United States Patent [19]
Rizzi

[11] Patent Number: 6,147,028
[45] Date of Patent: Nov. 14, 2000

[54] MODIFIED POROUS STARCH

[75] Inventor: George Peter Rizzi, Cincinnati, Ohio

[73] Assignee: The Procter & Gamble Company, Cincinnati, Ohio

[21] Appl. No.: 09/254,732

[22] PCT Filed: Sep. 10, 1997

[86] PCT No.: PCT/US97/15973

§ 371 Date: Mar. 11, 1999

§ 102(e) Date: Mar. 11, 1999

[87] PCT Pub. No.: WO98/10861

PCT Pub. Date: Mar. 19, 1998

Related U.S. Application Data

[60] Provisional application No. 60/025,933, Sep. 11, 1996.
[51] Int. Cl.[7] .............................. B01J 20/00; B01J 20/10; B01J 20/12; A61F 13/15; A61F 13/20
[52] U.S. Cl. .......................... 502/404; 502/407; 604/364; 604/375
[58] Field of Search .................................... 502/404, 407; 604/364, 375

[56] References Cited

U.S. PATENT DOCUMENTS

| | | | |
|---|---|---|---|
| 4,296,234 | 10/1981 | Mindt et al. | 536/47 |
| 4,959,341 | 9/1990 | Wallach | 502/404 |
| 4,985,082 | 1/1991 | Whistler | 502/404 |
| 5,445,678 | 8/1995 | Whistler | 127/67 |
| 5,676,660 | 10/1997 | Mukaida et al. | 604/375 |
| 5,801,116 | 9/1998 | Cottrell et al. | 502/404 |
| 5,986,166 | 11/1999 | Mukaida et al. | 604/368 |

FOREIGN PATENT DOCUMENTS 182296  5/1986  European Pat. Off. .

*Primary Examiner*—Mark L. Bell
*Assistant Examiner*—Patricia L. Hailey
*Attorney, Agent, or Firm*—Edward J. Milbrads; Rich S. Echler; Jerffrey V. Bamber

[57] ABSTRACT

The present invention relates to microporous starch granules surface coated with a hydrophobic agent said granules useful in absorbing hydrophobic malodorous materials either from the liquid or gas phase. The hydrophobic granules are useful in controlling the malodors associated with catmenials and hygienic undergarments as well as being useful for absorbing unwanted food and other environmental malodors.

9 Claims, No Drawings

MODIFIED POROUS STARCH

CROSS REFERENCE

This application claims priority under Title 35, United States Code 119(e) from Provisional Application Ser. No. 60/025,933, filed Sep. 11, 1996.

FIELD OF THE INVENTION

The present invention relates to a surface coated modified starch matrix useful for absorption of malodor. The present invention also relates to methods for absorbing hydrophobic materials from the air or aqueous matrices.

BACKGROUND OF THE INVENTION

The suppression or elimination of odors, particularly undesirable odors, has been the objective of countless investigations. Malodors have their genesis in many forms but those that are of most consequence to human beings are those involving occasional or repeated daily exposure. Of primary concern are those malodors that are caused by normal bodily functions, for example, the urine and feces odors associated with infants and the malodors associated with menses.

Cultural and aesthetic standards have influenced the permissible level of human and environmental malodors and control of these odors has been the focus of investigation for many centuries. In general, these investigations have been focused on either of two approaches, namely: (a) odor masking, in which a substance of strong yet relatively pleasant odor is introduced into the proximity of a less pleasant odor source with the intent of overburdening the olfactory receptors with the dominant pleasant odor, or (b) sequestering the undesired odorous substance in a non-volatile form either by chemical reaction, adsorption or absorption on a sorbent material exhibiting a preference for the odorous substance.

Odor masking, although effective in the short term, has certain limitations. First, masking does not remove or eliminate the source of the malodor. Secondly, when scents and perfumes are used to overcome malodors, the user must make sure an effective and constant level of masking agent is present to avoid too low a level of masking agent that may not be sufficient to cover-up the malodor. In turn, too high a level of masking agent may itself produce an undesirable effect. The premature depletion of the masking agent can be an additional concern.

Sequestration has thus become the method of choice for elimination and control of both human and environmental malodors. The more effective approach has been to sequester the undesired malodor primarily by adsorption.

By far the most commonly employed of the solid adsorbents are activated charcoal or active carbon, although silica gel, activated alumina, kieselguhr, Fullers earth and other clay minerals and zeolites, alone or in combination, have also been proposed as odor "adsorbents". In U.S. Pat. No. 4,437,429, to Goldstein et al., issued Mar. 20, 1984, the use of a hydrated zeolite in admixture with clay is proposed as being particularly useful for the control of odors from pet litter. Though it is observed that the use of zeolites by themselves as litter material has generally been unsuccessful due to their poor water adsorption properties as compared with clays. However, these absorbents are direct to methods of soaking up moisture or liquids whereas, described herein below, the present invention is directed to the absorption of volatile substances without the necessity to absorb any liquid carrier material.

The use by women during menstruation of sanitary napkins, pads, and panty liners has become common place. Although natural fluids produced during menstruation are suitably absorbed by the catamenial absorbent material thereby protecting clothing from damage, the problem of malodor persists. This is due in part to the fact that many chemical compounds responsible for malodor typically have very low odor detection thresholds and are perceptible at the part per million (ppm) level. In addition, may of these malodorous materials are hydrophobic easily partitioning out of the liquid phase as the fluids are absorbed by the catmenial substrate material.

It has now been surprisingly found that modified starch granules can be coated with surface modifying agents producing microporous hydrophobic granules that readily absorb malodorous agents even when the agents are in the "gaseous" state. For example, when menstrual fluid is absorbed onto a substrate, volatile low molecular weight compounds nevertheless can still escape into the gas phase resulting in the release of malodors. The modified starch granules of the present invention contain modified surfaces that absorb these and like malodors therefore removing them from the air.

Modification of porous starch granules by partial solubilisation with alpha-amylase for use as dusting powders and talc is described in European Patent Application 182,296, published May 28, 1986. However, the purpose of the modified starch granules is the complete absorption of moisture without concomitant caking.

Other modified starch materials have been described, for example, U.S. Pat. No. 4,985,082 to Whistler, issued Jan. 15, 1991, which discloses treated granular starches derivatized to enhance the absorptive properties. This patent discloses the specific use of interior crosslinking agents to strengthen the granules against collapse when too much moisture is absorbed. This patent relates to releasable containment of an absorbate whereas the present invention preferably does not release the volatile materials once absorbed.

BACKGROUND ART

Further publications related to porous modified substrates or starch hydrolysates are U.S. Pat. No. 5,445,678, Whistler, issued Aug. 29, 1995; Japanese Patent Applications 01157903 A and 01218882 A.

SUMMARY OF THE INVENTION

The present invention relates to an absorbent starch material suitable for absorbing volatile compounds having a hydrophobic affinity, comprising:

a) a partially hydrolyzed porous starch matrix; and
b) a siloxane surface modifying agent applied to the porous starch matrix.

It is a further object of the present invention to provide a method for removing volatile malodor compounds from a liquid comprising the step of contacting the fluid containing malodorous volatile compounds with the absorbent material of the present invention.

All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

Partially Hydrolyzed Porous Starch Matrices

The absorbent starch materials of the present invention comprise an enzyme modified starch granule treated with a surface modifying siloxane polymer. The starch granule is modified in that treatment of the granule affords a pore void volume of about 10% to about 65%, preferably from about 10% to about 50% more preferably from about 20% to about 40% the volume of the granule. Applied to this modified starch granule is a surface modifying siloxane polymer in an amount from about 0.01% to about 10%, preferably from about 0.1% to about 1%, more preferably from about 0.5% to about 0.75%, by weight of the starch. This enzyme modified starch granule constitutes the "hydrolyzed porous starch matrix" of the present invention.

The terms "porous starch" and "microporous starch" are used interchangeably throughout the description of the present invention and are taken to mean "starch or starch granules having been modified by a substrate, preferably and enzyme, resulting in the structural lattice of the granule having holes, pores or openings which allow smaller molecules to enter the interstices of the starch granules".

The starch granules suitable for modification and for use in the present invention may comprise any starch which is capable of modification to increase pore volume or surface area, for example, corn or potato starch, having a preferred particle size of from 10 to 50 micron. However, this invention is not limited the aforementioned particle size range. The source of starch granules for use in the present invention is discretionary to the formulator.

An example of porous starch granules suitable for use in the present invention are starch granules modified by treatment, usually by amylase enzymes, to increase the void volume and thereby producing a microporous starch matrix. Any of a wide variety of art-recognized alpha-amylase or glucoamylases including those derived from *Rhizopus niveus*, *Asperigillus niger*, and *Rhizopus oryzae* and *Bacillus subtilis* and alpha-amylases and glucoamylases of animal origin, can be used. Alpha-amylases having a fungal origin are especially suitable for use in the present invention. Preferred amyloglucosidases are Rhizopus sp. (Sigma A 7255) and *Asperigillus niger* (Sigma A 3042). A preferred alpha amylase is that derived from *Asperigillus oryzae* (Sigma A 0273). Bacterial alpha-amylases are also suitable for use in the present invention, for example, Sigma A 6380, NOVO LE17, NOVO SP722, NOVO SP690, including the alpha amylase derived from genetically engineered variants of Bacillus sp. such as NOVO SE22. Also suitable is the porcine pancreas amylase, Sigma A 4268. Most preferred are the fungal amylglucosidase from *Asperigillus niger* available from NOVO as AMG 300L.

Microporous starch granules prepared by the action of acid or amylase on granular starch are well known in the literature, see for example, Starch Chemistry and Technology, Whistler, Roy L., 2nd Edition, (1984), Academic Press, Inc. New York, N.Y. These methods and others, as well as those disclosed herein, are suitable for preparing a partially hydrolyzed porous starch matrix.

The duration of enzyme treatment necessary to produce microporous starch matrices suitable for use in accordance with this invention depends on a number of variables, including the source of starch, species and concentration of amylases, treatment temperature, and pH of the starch slurry. The progress of starch hydrolysis can be followed by monitoring the D-glucose content of the reaction slurry. In a preferred embodiment, the starch hydrolysis reaction is allowed to proceed until about 17 to about 20% of the starch has been solublized.

Siloxane Surface Modifying Agent

The silicone polymers useful for the present invention are those siloxanes that can be used to suitably coat the surface of the modified starch granules rendering the surface of the starch granules hydrophobic. In general, silicone denotes a synthetic polymer having the formula $$[R_n SiO(4-n)/2]_m$$

wherein n has the value from 1 to 3 and m is greater than or equal to 2. These materials contain a repeating silicon-oxygen backbone and have organic groups R attached to a significant proportion of the silicon atoms by silicon-carbon bonds. The terms "silicone" and "siloxane" are used interchangeably throughout the description of the present invention and are taken to mean the silicon containing polymers used to modify the surface of the starch granules. Further descriptions of silicones can be found in the literature, for example, Kirk-Othrner *Encyclopedia of Chemical Technology*, 3rd Ed. vol. 20, p. 922.

Preferred siloxane polymers suitable for use as a hydrophobic coating according to the present invention have the formula

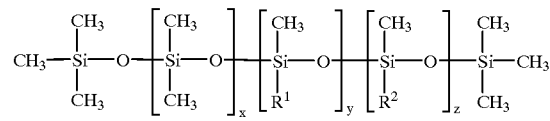

wherein $R^1$ units are hydrocarbyl units, preferably $C_2$–$C_{22}$ linear alkyl, $C_3$–$C_{22}$ linear alkenyl, $C_2$–$C_{22}$ branched alkyl, $C_3$–$C_{22}$ branched alkenyl, phenyl, benzyl, phenoxy, benzyloxy; $R^2$ units are —$(OR^3)_n R^4$ or —$(CH_2)_m (OR^3)_n R^4$ wherein $R^3$ is $C_2$–$C_{12}$ alkylene; $R^4$ is hydrogen, $C_2$–$C_{12}$ alkyl, —$NR^5 R^6$ wherein $R^5$ and $R^6$ are each independently $C_2$–$C_{22}$ linear alkyl, $C_3$–$C_{22}$ linear alkenyl, $C_2$–$C_{22}$ branched alkyl, $C_3$–$C_{22}$ branched alkenyl, phenyl, benzyl, phenoxy, benzyloxy, and mixtures thereof $R^4$ units are preferably hydrogen or methyl. The value of m is from 1 to 22; the value of n is from 1 to 22; the value of x is from 0 to about 10,000; the value of y is from about 0 to about 10,000; the value of z is from 0 to about 10,000.

$R^2$ units comprising —$(OR^3)_n R^4$ units can be formed from one or more different $R^3$ units. For example, —$(OR^3)_n R^4$ may be rewritten as —$(OR^3)_{n'}(OR^{3''})_{n''} R^4$ wherein n'+n"=n, for $R^2$ units having two types of alkyleneoxy units. In a like manner —$(OR^3)_n R^4$ may be rewritten as $(OR^{3'})_{n'}(OR^{3''})_{n''}(OR^{3'''})_{n'''} R^4$ wherein n'+n"+n'''=n when three different alkyleneoxy units comprise $R^2$. An example of —$(OR^3)_n R^4$ equal to —$(OR^{3'})_{n'}(OR^{3''})_{n''} R^4$ comprising both ethyleneoxy and propyleneoxy units has the formula

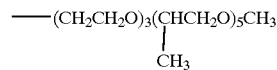

wherein n'+n"=n=8, $R^{3'}$ is ethyleneoxy, $R^{3''}$ is propyleneoxy and $R^4$ is methyl.

Examples of preferred siloxanes suitable for use in the present invention are the siloxanes available from Goldschmidt Chemical Corporation sold under the tradename ABIL®, for example, ABIL® AV 20–1000, ABIL® B 9800, ABIL®D B 9801, ABIL® WS 08, ABIL® WE 09.

The siloxane surface modifying agents are readily applied to the surface of the modified starch by contacting a sample of water-free starch with the siloxane dissolved in a suitable non-polar solvent such as toluene, xylene, hexane, and isopentane. However, this list of solvents is not meant to be inclusive of all solvents suitable for use in the practice of the present invention. The formulator may also employ mixtures of solvents.

Contacting surface modified porous starch granules of the present invention with an aqueous medium containing malodorous hydrophobic compounds will have the effect of removing the malodorous compounds from the aqueous medium with a minimal absorption of water. When used as such, the porous granules of the present invention are considered to be selectively extracting malodorous hydrophobic materials. Because the starch granules of the present invention are modified to have a highly hydrophobic surface area, the malodorous compounds have a higher affinity for the porous starch granules than for the surrounding aqueous-based media.

It is a typical practice for grocery stores, butcher shops and other retail handlers of fresh meat, poultry and fish to package the meat, poultry or fish product in a package or wrapper having a blood or other fluid absorbing article. Impregnating this absorbing article with the modified microporous starch granules of the present invention is another example of using the modified microporous starch granules to mediate the formation of malodorous materials within the present invention.

The present invention also consists of a method for absorbing a malodorous hydrophobic compound from an aqueous-based medium comprising the step of contacting the aqueous-based medium with a surface modified starch granule comprising a partially hydrolyzed porous starch matrix and a siloxane surface modifying agent applied to the porous starch matrix.

The term "aqueous-based medium" is defined as a fluid material the major liquid component of which is water. Examples of an aqueous-based medium are blood, urine, and feces. However, an aqueous-based medium can also comprise water that has been used to solublize a solid or to extract a solid material. For example, an aqueous-based medium once dried of all fluid including those volatile liquids other than water may be reconstituted with water to re-form the aqueous-medium.

The surface modified microporous starch granules of the present invention can also be applied to fabric, for example draperies, curtains, outerwear, etc. to absorb malodors that come into contact with the fabric. For example, cigarette smoke in a room may be suitably absorbed when the granules of the present invention are applied to the carpeting and other fabric (upholstery) within a room. Simple vacuuming of the granules removes the used particles containing the entrained malodors and then a fresh supply of granules can be applied at the convenience of the user.

The present invention also comprises a method for absorbing a hydrophobic material comprising the step of contacting the hydrophobic material having a ClogP greater than 1 with a surface modified absorbent comprising a partially hydrolyzed porous starch matrix and a siloxane surface modifying agent applied to the porous starch matrix.

The hydrophobic material which is removed may be a material that is not malodorous but is nevertheless undesirable for other aesthetic reasons. These hydrophobic materials typically have a ClogP greater than 1. The hydrophobic material having a ClogP greater than 1 may be a freely dispersed material in the air or the material may be dispersed in an aqueous-based medium.

The hydrophobic materials removable or irreversibly absorbable by the modified microporous surface coated starch granules of the present invention are characterized by the calculated logarithm of their octanol/water partition coefficient, ClogP. The octanol/water partition coefficient of a hydrophobic species is the ratio between its equilibrium concentration in octanol and in water. Since the partition coefficients are frequently large, they are more conveniently given in the form of their logarithm to the base 10, logP.

The logP of many hydrophobic species has been reported; for example, the Ponmona92 database, available from Daylight Chemical Information Systems, Inc. (Daylight CIS), contains many, along with citations to the original literature.

However, the logP values are most conveniently calculated by the "CLOGP" program, also available from Daylight CIS. This program also lists experimental logP values when they are available in the Pomona92 database. The "calculated logP" (ClogP) is determined by the fragment approach of Hansch and Leo (cf., A.

Leo, in Comprehensive Medicinal Chemistry, Vol. 4, C. Hansch, P. G. Sammens, J. B. Taylor and C. A. Ransden, Eds., p. 295, Pergamon Press, 1990, incorporated herein by reference). The fragment approach is based on the chemical structure of each hydrophobic compound, and takes into account the numbers and types of atoms, the atom connectivity, and chemical bonding. ClogP values are the most reliable and widely used estimates for octanol water partitioning. It will be understood by those skilled in the art that experimental log P values could also be used. Experimental log P values represent a less preferred embodiment of the invention. Where experimental log P values are used, the one hour log P values are preferred.

For example, the surface modified microporous starch granules of the present invention may be placed in the path of free flowing air which contains malodorous compounds or compounds that have a ClogP value greater than 1, preferably greater than 2, more preferably greater than 3, most preferably greater than 4. The surface modified starch granules of the present invention, because of the high pore volume and irreversible nature of the hydrophobic absorption, can be used to absorb unwanted odor that form on a continuing basis, for example, the starch granules can be placed in a refrigerator where the commingling of food aromas or malodors odors is undesirable.

The materials of the present invention absorb hydrophobic compounds which are typically responsible for malodor from liquid or aqueous-based media. The presence of a hydrophobic liquid or other aqueous based fluid does not diminish or prohibit the absorption of these malodorous compounds.

The relative hydrophobicity of the modified starch granules can be measured using one or more techniques common to the art. For example, modified corn starch and modified corn starch coated with a siloxane polymer are heated in an oven. The samples are removed and placed in a constant humidity environment and are allowed to re-absorb water from the atmosphere. The difference in the amount of re-absorbed water between the two samples can readily serve as a basis for expressing relative hydrophobicity. The formulator may also correlate this difference in water re-absorption with the amount of siloxane that effectively coats the modified porous starch granules thereby adjusting the amount of siloxane polymer to fit the desired hydrophobicity.

The following non-limiting examples illustrate the preparation and use of the siloxane coated modified starch granules of the present invention for control of malodor.

EXAMPLE 1

A 22 L round-bottom flask is charged with acetic acid (17.17 mL), sodium acetate/trihydrate (27.21 gm), calcium chloride dihydrate (0.118 gm) and sufficient distilled water to make up a 4.0 L solution. With gentle mixing powdered corn starch is added (1.0 kg) followed by AMG300L enzyme solution (40.0 mL) (NovoNordisk). Stirring is continued for 30 hours at 23° C. The resulting solution is filtered through a double thickness of Whatman No. 4 paper and the solid product is washed with about 2 L of water then with about 500 mL of ethanol. The product is air dried and yields 724 gm. The modified starch is then oven dried for about 5 hours in an oven set at 110° C. to yield 648 gm of an odorless, white, free-flowing powder. The product is used for coating with siloxanes without further need for purification.

EXAMPLE 2

Dissolve ABIL AV-1000 siloxane (Goldschmidt) (15 gm) in toluene (150 mL). Porous corn starch (20% void volume, ~0.20 cc/gm, prepared according to U.S. Pat. No. 4,985,082) is pre-dried at 110° C. for 4 hours. A sample of the starch (30 gm) is added to the solution of ABIL and heated to a boil for about 2 minutes then cooled to room temperature. The slurry is isolated by filtration, dried in air, then dried at 100° C. for 19 hours to yield a free flowing solid suitable for direct use in a catamenial, diaper or in conjunction with other malodor producing materials.

EXAMPLE 3

Dissolve ABIL AV-1000 siloxane (Goldschmidt) (15 gm) in isopentane (150 mL). Porous corn starch (20% void volume, ~0.20 cc/gm, prepared according to U.S. Pat. No. 4,985,082) is pre-dried at 110° C. for 4 hours. A sample of the starch (30 gm) is added to the solution of ABIL and heated to a boil for about 2 minutes then cooled to room temperature. The slurry is isolated by filtration, dried in air, then dried at 100° C. for 19 hours to yield a free flowing solid suitable for direct use in a catamenial, diaper or in conjunction with other malodor producing materials.

U.S. Pat. No. 5,308,346, Sneller et al., issued May 3 1994, discloses a unitary disposable absorbent article having an elasticized side flap by operatively associating an elastic member on both the upper surface and lower surface of the side flap. These articles may be used as a catamenial or an incontinence article. The modified starch granules prepared according to Examples 2 or 3 are added to the absorbent substrate that comprises the unitary disposable absorbent article in an amount at least 10% by weight of the absorbent material. The resulting modified disposable absorbent article is suitable for use by a wearer wherein diminished malodor is desirable.

What is claimed is:

1. A material for absorbing a hydrophobic compound comprising:

a) a partially hydrolyzed porous starch matrix, the starch having a surface; and b) a siloxane surface modifying agent applied to the porous starch matrix, wherein the modifying agent renders the surface of the starch substantially hydrophobic.

2. The absorbent material according to claim 1 wherein the porous starch matrix comprises starch granules partially hydrolyzed with an amylase enzyme.

3. The absorbent material according to claim 2 wherein the porous starch is corn starch, potato starch, or mixtures thereof.

4. The absorbent material according to claim 3 wherein the porous starch is corn starch.

5. The absorbent material according to claim 4 wherein the siloxane surface modifying agent has the formula

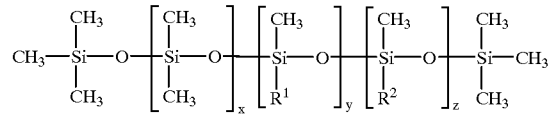

wherein $R^1$ units are $C_2$–$C_{22}$ linear alkyl, $C_3$–$C_{22}$ linear alkenyl, $C_2$–$C_{22}$ branched alkyl, $C_3$–$C_{22}$ branched alkenyl, phenyl, benzyl, phenoxy, benzyloxy; $R^2$ units are —$(OR^3)_n R^4$ or —$(CH_2)_m (OR^3)_n R^4$ wherein $R^3$ is $C_2$–$C_{12}$ alkylene; $R^4$ is hydrogen, $C_1$–$C_{12}$ alkyl, or $NR^5 R^6$, wherein $R^5$ and $R^6$ are each independently $C_2$–$C_{22}$ linear alkyl, $C_3$–$C_{22}$ linear alkenyl, $C_2$–$C_{22}$ branched alkyl, $C_3$–$C_{22}$ branched alkenyl, phenyl, benzyl, phenoxy, benzyloxy, and mixtures thereof; the value of m is from 1 to 22; the value of n is from 1 to 22; the value of x is from 0 to about 10,000; the value of y is from about 0 to about 10,000; the value of z is from 0 to about 10,000.

6. The absorbent material according to claim 5 wherein $R^4$ units are selected from the group consisting of hydrogen, methyl, and mixtures thereof.

7. A method for absorbing a hydrophobic compound from an aqueous-based medium comprising the step of contacting the aqueous-based medium with a surface modified microporous starch granule comprising a partially hydrolyzed porous starch matrix and a siloxane surface modifying agent applied to the porous starch matrix, wherein the modifying agent renders the surface of the starch granule substantially hydrophobic.

8. The method according to claim 7 wherein the porous starch matrix is corn starch.

9. A method for absorbing a hydrophobic material comprising the step of contacting the hydrophobic material having a ClogP greater than 1 with an absorbent material comprising a partially hydrolyzed porous starch matrix and a siloxane surface modifying agent applied to the porous starch matrix, wherein the modifying agent renders the porous starch matrix substantially hydrophobic.

\* \* \* \* \*